(12) United States Patent
Chawla et al.

(10) Patent No.: US 6,500,955 B1
(45) Date of Patent: Dec. 31, 2002

(54) ONE POT SYNTHESIS OF [2,8-BIS (TRIFLUOROMETHYL)-4-QUINOLINYL]-2-PYRIDINYLMETHANONE, A MEFLOQUINE INTERMEDIATE

(75) Inventors: Harmander Pal Singh Chawla, S.A.S. Nagar (IN); Perminder Singh Johar, Chandigarh (IN); Alka Mittal, S.A.S. Nagar (IN); Ram Avtar Meena, S.A.S. Nagar (IN); Villendra Singh Negi, S.A.S. Nagar (IN)

(73) Assignee: National Institute of Pharmaceutical Education and Research, Punjab (IN)

( * ) Notice: Subject to any disclaimer, the term of this patent is extended or adjusted under 35 U.S.C. 154(b) by 0 days.

(21) Appl. No.: 10/058,304

(22) Filed: Jan. 30, 2002

(30) Foreign Application Priority Data

Feb. 2, 2001 (IN) ..................................... 129/DEL/2001

(51) Int. Cl.[7] ............................................. C07D 401/06
(52) U.S. Cl. ...................................................... 546/168
(58) Field of Search ........................................... 546/168

(56) References Cited

U.S. PATENT DOCUMENTS

| 4,327,215 A | 4/1982 | Hickmann et al. |
| 4,429,130 A | 1/1984 | Hickmann et al. |

FOREIGN PATENT DOCUMENTS

| DE | 37 09 841 A1 | 10/1988 |
| IN | 170918 | 6/1992 |
| IN | 170919 | 6/1992 |

Primary Examiner—Patricia L. Morris
(74) Attorney, Agent, or Firm—Oliff & Berridge, PLC

(57) ABSTRACT

The present invention provides a simple single step process for the preparation of [2,8-bis(trifluoromethyl)-4-quinolinyl]-2-pyridinylmethanone, comprising the step of condensing a halo-quinoline with an alpha-picolyl derivatives in the presence of a solvent, a base and a phase transfer catalyst at −10° C. to +90° C.

23 Claims, 4 Drawing Sheets

1

2

Figure 1:
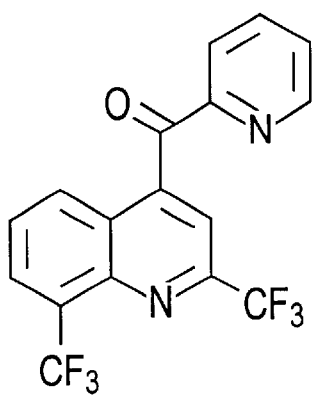
Figure 1:
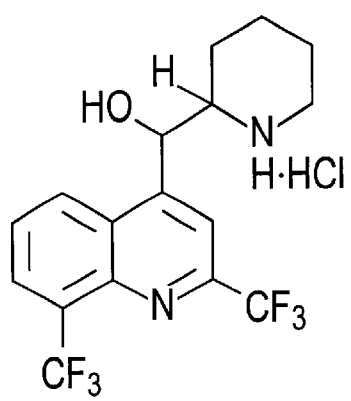
Figure 1:
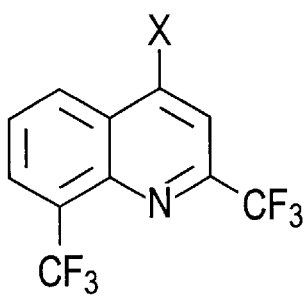
Figure 1:
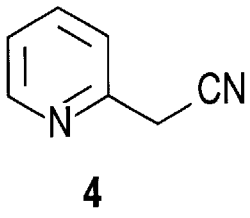
Figure 1:
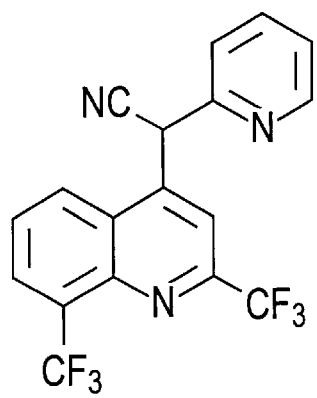
Figure 1:
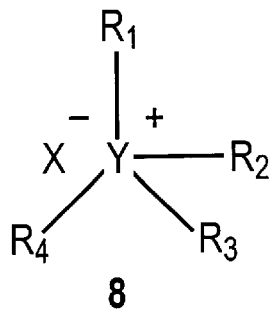

3 X = Cl
6 X = Br
7 X = I

4

5

8

ONE POT SYNTHESIS OF [2,8-BIS (TRIFLUOROMETHYL)-4-QUINOLINYL]-2-PYRIDINYLMETHANONE, A MEFLOQUINE INTERMEDIATE

FIELD OF THE INVENTION

The present invention relates to an improved process for the preparation of [2,8-bis(trifluoromethyl)-4-quinolinyl]-2-pyridinylmethanone, having structural formula 1, which is an important drug intermediate, more particularly for the preparation of the anti-malarial drug mefloquine having structural formula 2.

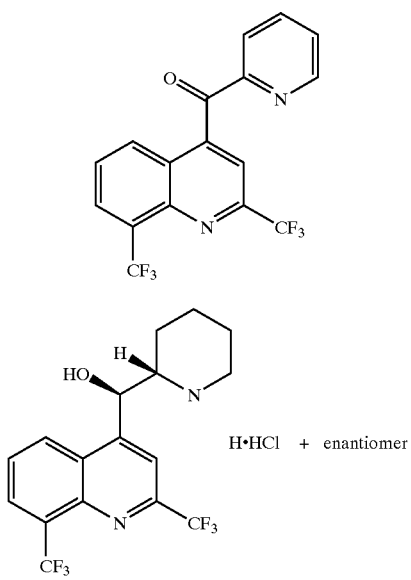

BACKGROUND OF THE INVENTION

Malaria ranks third among the major infectious diseases after acute respiratory infections and tuberculosis. About 2.5 million deaths occur per year due to malaria, 90% occurring in Africa mostly caused by *Plasmodium falciparum*. Children under the age of 5 years are hit by malaria. Malaria kills one child every 12 seconds. Human environmental changes such as road building, mining, deforestation and new agricultural and irrigation projects have created new breeding sites and thus contribute to spread of malaria. Malaria has re-emerged in areas where it had been eradicated e.g. Koreas, Central Asian republics.

Wide spread prevalence of malaria and emergence of drug resistant *Plasmodium falciparum* have enhanced the importance of mefloquine as a highly effective anti-malarial agent.

Resistance of *P. falciparum* to chloroquine, one of oldest, cheapest and most commonly used drugs, was first detected in 1960. Resistance of sulfadoxine/pyrimethamine, the main alternative to chloroquine is wide spread in South-east Asia and South America. It is being recommended that combination of drugs should be used to slow down the development of drug resistance. Mefloquine has emerged as an important drug to be used in these combinations. An important intermediate in the preparation of mefloquine is methanone of formula (1).

In the prior art, the methanone (1) has been prepared through various routes, all of which suffer from one or more shortcomings as listed below:

Methanone was first prepared [Ohnmacht, C. J., Palei, A. R. and Lutz, R. E., J. Med. Chem. 14, p. 926, 1971] by the reaction of 2-pyridyl lithium (prepared in situ from 2-bromo pyridine and n-butyl lithium) with 2,8-bis(trifluoromethyl)-quinoline-4-carboxylic acid. Apart from being expensive, the use of butyl lithium on large scale always poses the problems of fire and explosion hazards.

As a variant of this method, 2-pyridylmagnesium bromide was used for the synthesis instead of 2-pyridyl lithium [Hickmann, E., Oeser, H. -G. and Moebius, L. U.S. Pat. No. 4,327,215, 1982]. The organomagnesium complexes also have fire and explosion hazards associated with them.

An alternative to the method taught by Hickmann, E., Oeser, H. -G. and Moebius, L. U.S. Pat. No. 4,327,215 1982, 2,S-bis(trifluoromethyl)-quinoline-4-carboxylic acid has been replaced by 4-cyano-2,8-bis(trifluoromethyl)-quinoline. Methanone of formula 1 was obtained in only moderate yields. [Nagesheswar Y. V. D., Meshram H. M., Prasad A. R., Hashim S. R. and Sattur P. B. R., Indian IN 170919 (1992)]. The method still uses an organometallic reagent which carries fire and explosion hazards on scaleup.

In another process, methanone of structural formula 1 has been obtained by the reaction of 4-lithio-2,8-bis (trifluoromethyl)-quinoline [prepared in situ from 4-bromo-2,8-bis(trifluoromethyl)-quinoline and n-butyl lithium] and 2-cyanopyridine, [Haenni, R. and Kuendig, W., Ger Offen. DE 3709891 (1987)]. The organo lithium intermediate obtained is hazardous.

As a modification of the route described heretofore [Haenni, R. and Kuendig, W., Ger Offen. DE 3709891 (1987)] 2,8-bis(trifluoromethyl)-quinolinylmagnesium bromide [prepared in situ from 4-bromo/iodo-2,8-bis (trifluoromethyl)-quinoline and magnesium] was utilized instead of the 4-lithio derivative. [Nagesheswar Y. V. D., Meshram H. M., Prasad A. R., Hashim S. R. and Sattur P. B. R., Indian IN 170918 (1992)]. The disadvantage of the method includes hazardous nature of organomagnesium intermediate and low yields.

In yet another process 4-bromo-2,8-bis(trifluoromethyl)-quinoline of formula (6) on reaction with 2-pyridylacetonitrile (4) in presence of concentrated NaOH, DMF and tetra butylammonium chloride at an ambient temperature under nitrogen atmosphere furnished α,2-pyridinyl-2,8-bis(trifluoromethyl)-4-quinolineacetonitrile of formula (5). [Hickmann, E. and Oeser, H. -G. U.S. Pat. No. 4,429,130 (1984)]. In the second step, the acetonitrile of formula (5) is converted to methanone of formula (1) by oxidation with hydrogen peroxide in acetic acid. This method suffers from the following disadvantages (1) the first step is carried out in presence of a base and dimethylformamide, whereas second step of oxidation is carried out in acetic acid medium (2) dimethylformamide (DMF) is incompatible with hydrogen peroxide used in the oxidation step [Hickmann, E., Oeser, H. -G. U.S. Pat. No. 4,429,130 (1984)] this necessitating the isolation of intermediate acetonitrile of formula 5.

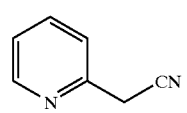

(4)

-continued

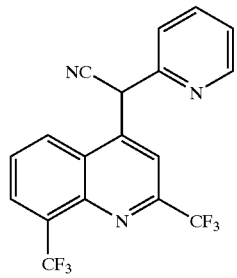

(5)

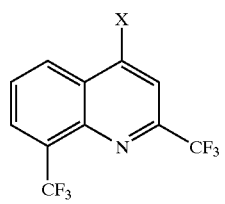

(6)

3 X = Cl
6 X = Br
7 X = I

As a modification of prior art [Hickmann, E. and Oeser, H. -G. U.S. Pat. No. 4,429,130 (1984)] 4-chloro-2,8-bis (trifluoromethyl)quinoline of formula 3, sodium hydride, dry toluene-dry DMF and 0° C.–10° C. temperature conditions were utilized instead of 4-bromide derivative concentrated NaOH, DMF and tetrabutylammonium chloride at room temperature conditions respectively [Solange A., Tetrahedron 47, 7609 (1991)]. Second step reagents were same as in prior art [Hickmann, E., and Oeser, H. -G. U.S. Pat. No. 4,429,130 (1984)]. This method suffers from the following disadvantages (1). The first step requires the use of inert and anhydrous conditions and the use of sodium hydride which can pose problems during scale up operations due to fire and explosion hazard. (2) In order to carry out second step, acetonitrile derivative (5) needs to be isolated.

Thus the prior art has no method whereby the intermediate methanone of formula (1) of the drug mefloquine of formula (2) can be prepared in a single pot and without the use of hazardous chemicals. There was a long felt need in the art to develop a process which is safe, economical and easy to follow.

OBJECTS OF THE INVENTION

The main object of the present invention is to provide a one pot, single step simple and economical process for the preparation of methanone of structural formula (1) from haloquinoline of the formula (3) and 2-pyridylacetonitrile of formula (4).

Yet another object of the present invention is to provide a process for the preparation of methanone of formula (1) from an intermediate of formula (5) without the use of hazardous chemicals.

Still another object is to provide an improved process, which obviates the use of expensive anhydrous solvents or hazardous reagents in the preparation of methanone of formula 1.

Another object is to provide a process wherein the intermediate acetonitrile derivative of the formula (5) need not be isolated before oxidation.

Yet another object is to provide a process wherein the steps can be conveniently carried out sequentially in the same reaction vessel making it a one-pot process.

SUMMARY OF THE INVENTION

The invention provides a simple single step process for the preparation of [2,8-bis(trifluoromethyl)-4-quinolinyl]-2-pyridinylmethanone (I), comprising the step of condensing a halo-quinoline with an alpha-picolyl derivative in the presence of a solvent, a base and a phase transfer catalyst at −10° C. to +90° C. to obtain an intermediate acetonitrile derivative of formula (5), which is oxidised in situ to methanone derivative of formula (1).

BRIEF DESCRIPTION OF ACCOMPANYING DRAWINGS

FIG. 1: represents the structural formulae of the compounds methanone (1), mefloquine hydrochloride (2), 2-pyridylacetonitrile of formula (4), α,2-pyridinyl-4-quinolineacetonitrile (5) and haloquinolines 3, 6 and 7.

Figure 2:
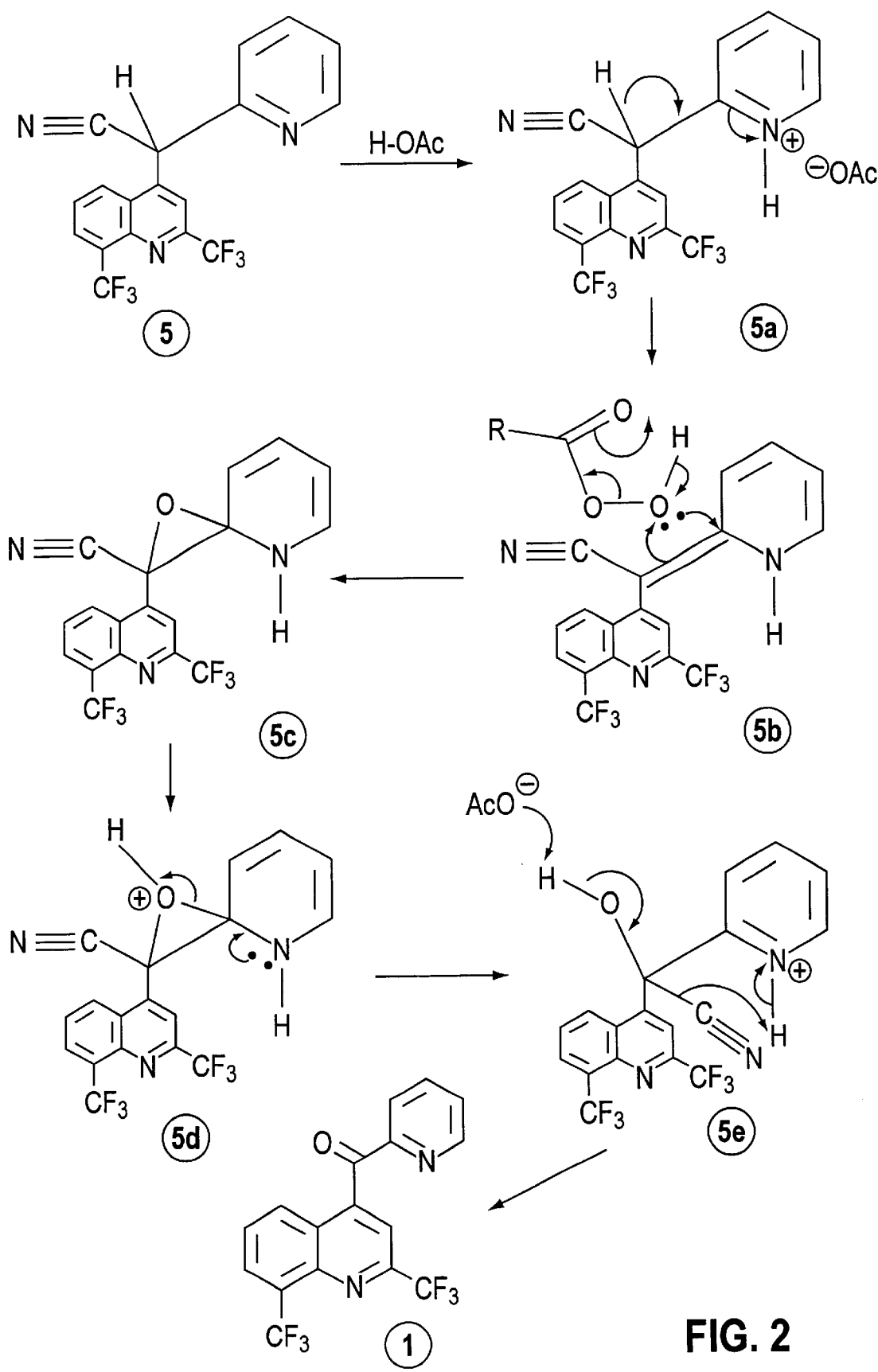

FIG. 2: represents the mechanism of the prior art process.

Figure 3:
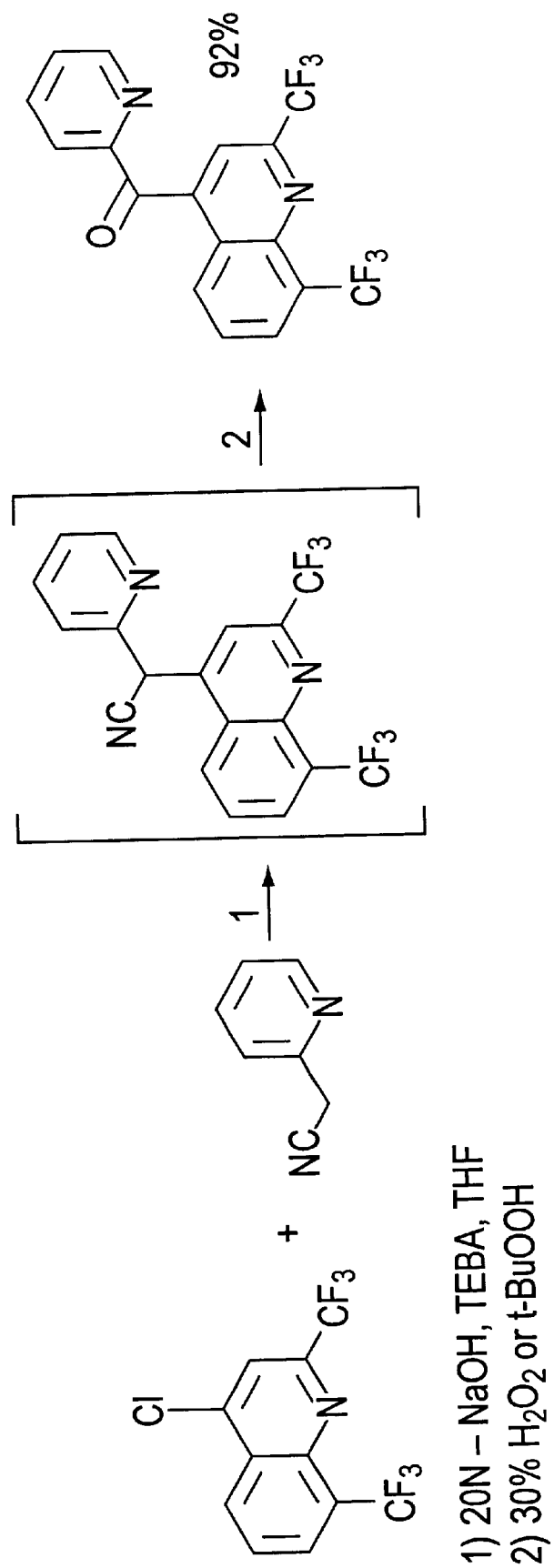

FIG. 3: represents the scheme of the process of the invention.

Figure 4:
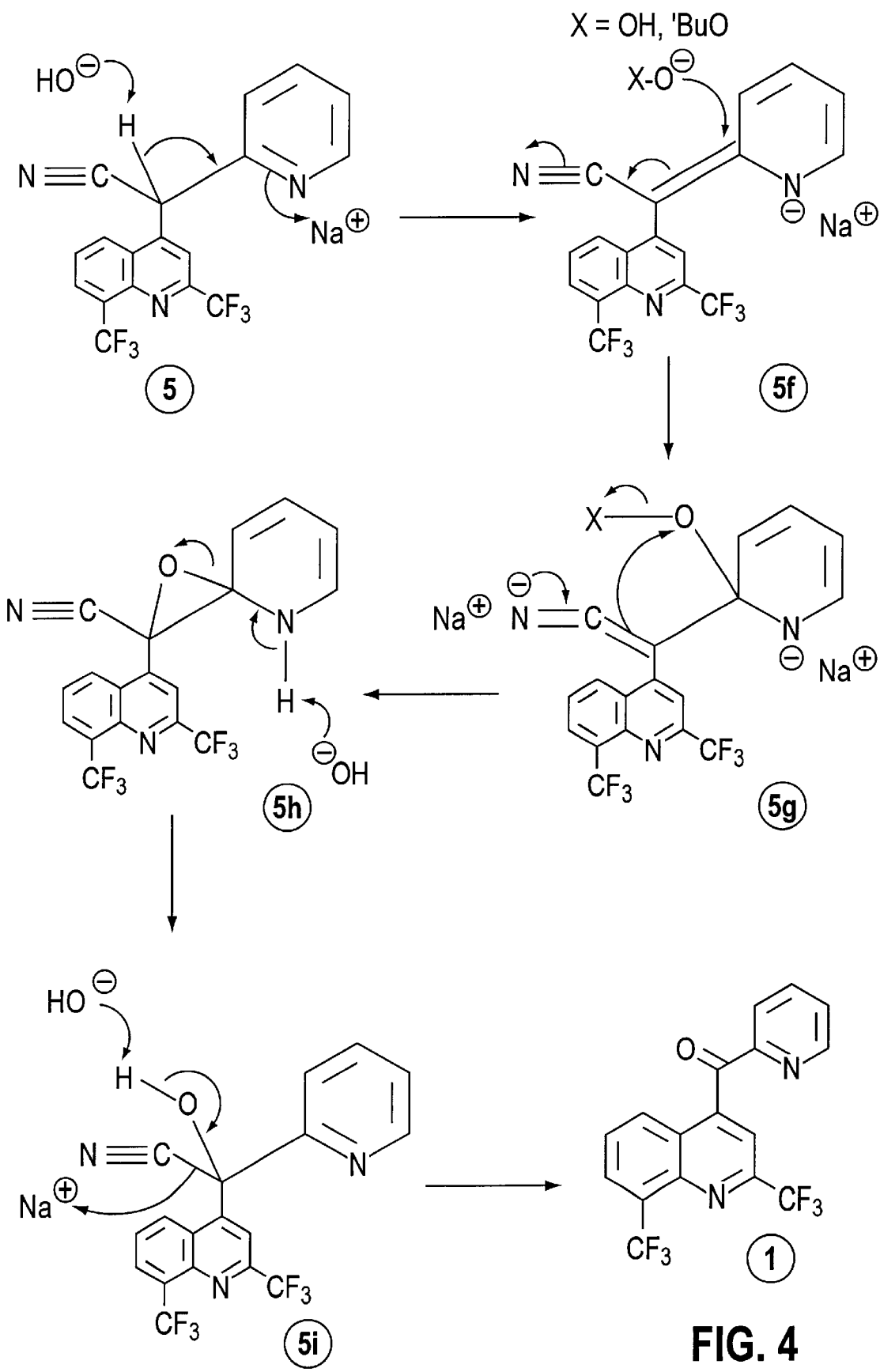

FIG. 4: depicts the mechanism of reaction of the present invention.

DETAILED DESCRIPTION OF THE INVENTION

In an embodiment of the present invention provides a process for the preparation of methanone of formula 1, the said process comprising steps of:

(a) condensing a halo-quinoline with an α-picolyl derivative in the presence of an organic solvent, a base and a phase transfer catalyst at −10° to +90° C.;

(b) adding an oxidising agent to the reaction mixture of step (a) containing the acetonitrile derivative of formula (5) at −10° to +90° C.;

(c) cooling the reaction mixture of step (b) and neutralising with any suitable acid followed by extraction with an organic solvent.

(d) removing the organic solvent of step (c) and crystallizing the methanone of formula (1).

In an another embodiment, the entire process described above is carried out in the same vessel, without the need to isolate the acetonitrile intermediate of structural formula (5). The process is thus an improvement over all existing and known methods. The reaction scheme is depicted in sheet No. 3.

A brief account of the mechanism of oxidation step of the prior art process and the process of present invention will enable one to understand the subtle difference in this process step, which is described herein below:

The current process being distinctly different from the prior art by performing the oxidation of the intermediate acetonitrile derivative in a basic medium and also enabling it to be a one pot process for the synthesis of methanone compound of formula (1). The prior art process especially U.S. Pat. No. 4,429,130 teaches that haloquinolines must first be condensed with pyridyl derivatives like 2-pyridylacetonitrile with 4-bromo-2,8 bis-trifluoromethyl-quinoline, to obtain compound of formula (5) which is isolated and then treated with acetic acid/hydrogen peroxide combination to obtain methanone of formula (1). The process is lengthy and requires change of reactor. The plausible mechanism of the reaction taught by this U.S. patent is depicted in FIG. 2. It is a typical acid catalyzed epoxidative oxidation, wherein the reacting species is peracetic acid ($CH_3COOOH$) generated by the reaction of acetic acid and $H_2O_2$. The nitrile 5 tautomerizes to form compound (5b) via compound (5a). The exocyclic double bond of compound (5b) is electron rich and this compound (5b) reacts quickly with peracetic acid to give the epoxide of formulae (5c) which rearranges rapidly via (5d) to form the cyanohydrin compound (5e), which further on elimination of HCN gives the required ketone 1. In this reaction, peracetic acid provides an electrophilic centre at oxygen atom, which is attacked by the α carbon to the nitrile group.

This is the applicant's finding that the entire reaction of formation of methanone (1) from intermediate acetonitrile derivative (5) can be effectively performed in one reaction pot itself by adding appropriate oxidizing agent. This results in the formation of compound (5i) i.e. cyanohydrin compound. This compound decomposes in situ to provide methanone of formula (1). This is achieved by using the solvent THF resulting in in situ generation of monosodium salt of hydrogen peroxide instead of peracetic acid of the prior art. The reaction of the invention is a base catalyzed reaction, wherein the base (OH⁻) tautomerises the proton α to the nitrile group of (5) to the α, β unsaturated nitrile containing compound (5f). Compound (5f) (which may partly be existing as compound (5b) reacts quickly with sodium hydrogen peroxide or sodium tertiary butyl peroxide to give the epoxide compound (5h) via the peroxide intermediate 5g. The epoxide (5h) rapidly rearranges with the help of the base (OH⁻) to form cyanohydrin (5i), which undergoes elimination of HCN to give the required ketone of formula (1). The oxidising agent used in this reaction acts as a nucleophilic reagent. It attacks the β carbon of compound (5f) to form the nitrile group. The oxidising agent acts on compound (5f) adds on to the α-β-unsaturated moiety at β-position and ultimately leads to formation of an epoxy derivative having formula (5h) via peroxide intermediate (5g). The compound (5g) finally becomes ketone of formula (1) via (5i). The exact mechanism of the reaction of the invention is shown in sheet no. 4. These changes result in combination of the 2 steps into one step. Sequential addition of reagents for the two steps and isolation of α,2-pyridinyl-2,8-bis(trifluoromethyl)-4-quinolineacetonitrile of formula (5) which is essential in the prior art [Hickman, E., and Oeser, H. -G. U.S. Pat. No. 4,429,130 (1984); Solange A. Tetrahedron 47, 7609 (1991)] is also eliminated by the process of the invention.

In still yet another embodiment, the starting compound is a 4-chloroquinoline derivative (3) selected out of the group of 4-haloquinoline derivatives. Other known quinoline derivatives may also be used. The process is, in fact, applicable to such derivatives.

In an yet another embodiment, the haloquinoline is condensed with an α-picolyl derivative, such as 2-pyridyl-acetonitrile of formula (4), pyridyl-acetic acid esters, α-nitro-2-picoline etc. the amount of this material may vary from 0.5 to 3.0 moles of haloquinoline used.

In an yet another embodiment, the reaction is preferably carried out in the presence of a solvent system capable of dissolving or dispensing the reactants and facilitating control of reaction temperature. Generally, the materials are dissolved in solvent of medium polarity. Any medium polar solvent such as tetrahydrofuran, diethyl ether, dioxane, 1,2-dichloroethane, 1,2-dichloromethane, chloroform, toluene, dimethyl formamide, dimethyl sulphoxide, etc. can be used as solvents. Ethers, chlorohydrocarbons and similar polar solvents may also be used in the reaction. The preferred organic solvent is tetrahydrofuran.

In an yet another embodiment, the organic solvent used in different steps of the process may be same or different.

In an yet another embodiment, the quantity of solvent used is not critical. But it must be taken in an amount such that it does not radically affect the yield of methanone. The quantity may be in the range of 1:1 to 1:10 of haloquinone used.

In an yet another embodiment, the base used in the process is generally a powdered solid or 10% to saturated solution of hydroxides, carbonates or acetates of alkali or alkaline earth metals such as NaOH, KOH, magnesium hydroxide, sodium carbonate, potassium carbonate, acetates of sodium potassium or calcium, etc. the amount of the base may be 5 to 10 times in excess of quinoline or equivalent to the amount of haloquinoline. Generally, the reaction is found to yield best results when the amount of base and quinoline used is in the range of 5:1.

In an yet another embodiment, the phase transfer catalyst in the reaction play the role of transferring the carbonion generated from pyridylacetonitrile represented by formula (4) or its analogues. The amount of this catalyst may vary from 1–10 mole %. The phase transfer catalyst may be selected from tetraalkylammonium or phosphonium salt of formula (8) wherein Y is nitrogen or phosphorous and $R^1$, $R^2$, $R^3$ and $R^4$ are identical or different substituents and can be alkyl groups with carbon 1 to 20 and X is Cl⁻, Br⁻, I⁻, $HSO_4^-$ or other anions derived from inorganic acids such as sulphuric acid, phosphoric acid or tetrafluoroboric acid.

In yet another embodiment, the oxidising agent plays a very important role in the reaction. The oxidation in step (ii) is effected by introducing an oxidising agent capable of providing a hydroperoxide ion or alkyl or cycloalkyl peroxide ion. Suitable oxidising agents for this purpose may be such as tertiary butylhydroperoxide, tertiary amyl hydroperoxide or hydrogen peroxide, etc. Examples of organic hydroperoxides useful in the present invention include cumene hydroperoxide; ethylbenzene hydroperoxide; cyclohexane hydroperoxide; methylcyclohexane hydroperoxide; pinane hydroperoxide; tetrahydronaphthalene hydroperoxide; isobutylbenzene hydroperoxide; isopropyl hydroperoxide; and ethylnaphthalene hydroperoxide. Mixtures of organic hydroperoxides may also be employed in the present invention. The amount of the oxidising agent added may be 1 to 5 mole equivalents with respect to haloquinoline.

In still yet another embodiment, the entire reaction is effected at −10 to +90° C. although maximum yield of methanone (1) is observed when the temperature is in the range of 45–60° C. As said earlier, the reaction conditions of the present invention have been so designed, that it can be effectively controlled and the entire reaction occurs in a single reactor without the need to use separate reactors. Once the reaction has progressed to the desired degree, the end product, i.e. the ketone can be removed by using conventional methods such as extraction, centrifugation, filtration etc.

In a yet another embodiment, the acids used for neutralization are selected from the group of mineral acids or organic acids, the preferred acid being ortho-phosphoric acid.

The invention is described by the following examples, which should not be construed as limitations on the inventive scope.

EXAMPLE 1

Synthesis of [2,8-bis(trifluoromethyl)-4-quinolinyl]-2-pyridinylmethanone (1)

In a round bottom flask (100 ml, 4 necked) equipped with a thermometer, water condenser, and a mechanical stirring unit, were placed 4-chloro-2,8-bis(trifluoromethyl)quinoline (3), (0.0385 mole, 11.52 g), 2-pyridylacetonitrile (4) (0.0423 mole, 5.0 g), benzyltriethylammonium chloride (0.26 g, 3 mole %), tetrahydrofuran (THF) (35 ml) and aq NaOH (20N, 9.63 ml, 0.192 moles). On stirring the colour of the solution became cherry red. The reaction temperature was increased to 50° C. and stirred for further 1 hour. Monitoring of the reaction mixture by thin layer chromatography (TLC) or gas liquid chromatography (GLC) indicated complete consumption of 4-chloroquinoline (3) to give nitrile (5). The reaction temperature was lowered to 20°–25° C. followed by addition of 30% $H_2O_2$ (13 ml, 0.1154 moles) maintaining 20°–25° C. and stirred at this temperature for one hour. TLC & GLC monitoring indicated complete coversion of nitrile compound (5) to compound (1). Reaction mixture was cooled to 0°–5° C. and neutralized by ortho-phosphoric acid (85% aq., 4.5 ml). THF was distilled off, followed by addition of water (30 ml) and extraction with toluene (50 ml×3). The crude product was crystallized from isopropanol to obtain compound (1). [Yield=13.17 gm (92%)]

| | |
|---|---|
| m.p | = 123° C., 1.m.p. = 113°–116° C.; 128°–129° C. [Hickmann, E., and Oeser, H. G. US 4429130 (1984)] |
| IR (cm$^{-1}$, KBr) | = 1685, 1583, 1429, 1322, 1126, 884, 750, 650 |
| NMR (300 MHz, δ J=Hz, CDCl$_3$) | = 8.63-1H, bd, J=4.67; 8.37-1H, d, J=7.89; 8.20-1H, d, J=7.23; 8.13-1H, d, H=8.56; 8.03-1H, dt, J=1.64, 7.75, 7.91-1H, s; 7.70-1H, t, J=7.87; 7.56-1H, m; |

EXAMPLE 2

Synthesis of [2,8-bis(trifluoromethyl)-4-quinolinyl]-2-pyridinylmethanone (1)

Repeating the procedure in Example 1 using aqueous tertiary butyl hydroperoxide, 70% (0.0577 mole, 7.43 ml) instead of hydrogen peroxide. Yield of compound (1) is 13.32 gm (93%). IR and NMR are identical with those of the product obtained in example 1.

EXAMPLE 3

Synthesis of α, 2-pyridinyl-2,8-bis(trifluoromethyl)-4-quinolineacetonitrile of formula (5)

4-chloro-2,8-bis(trifluoromethyl)quinoline (3), (0.0385 mole, 11.52 g), 2-pyridyl acetonitrile 4 (0.0423 mole, 5.0 g). NaOH (20N, aq. 9.63 ml, 0.192 moles), (THF) (35 ml) and benzyltriethylammonium chloride (0.26 g, 3 mole %), were reacted as described in Example 1. After consumption of compound (3), the reaction mixture was cooled to 0°–5° C. and neutralized by ortho-phosphoric acid (85% aq., 4.5 ml). THF was distilled off, water (30 ml) added and extracted with toluene (50 ml×5). All extracts were combined and solvent distilled off. The crude product was crystallized from toluene/hexane. Yield=14.52 gm (99%),

| | |
|---|---|
| m.p. | = 164° C.; 1m.mp. = 1.62°-165° C. [Hickmann, E., and Oeser, H. G. US 4429130 (1984)] |
| IR (cm$^{-1}$, KBr) | = 2881, 2244, 1589, 1518, 1473, 1321, 1139, 1115, 840, 772 |
| NMR (300 MHz, δ | = 8.6-1H, bd, J=4.8, 8.42-1H, d, J=8.6; 8.19-1H, d, J=7.3; 7.75-2H, t, J=7.8; = 7.44-1H, d, J=7.9, 7.3-1H, dd, J=4.9, 6.7; 6.061H, s. lit. MNR(DMSO-d$_6$); 7.11-14, s, 8.34-1H, s; 7.3–8.8, |
| J = Hz, CDCl$_3$ | m. [Solange Adam, CA: 116.20917w (1992); Tetrahedron 47 (36), 7609, 7614, (1991)]. |

EXAMPLE 4

Synthesis of [2,8-bis(trifluoromethyl)-4-quinolinyl]-2-pyridinyl-methanone of formula 1

Nitrile compound (5) (14.52 g, 0.03811 mole), NaOH (20N, aq. 7.45 ml, 0.149 moles), THF (35 ml) and 30% $H_2O_2$ (13 ml, 0.1154 mole) added at 20°–25° C. and stirred for 1 hour. Work up is same as described in Example 1. Yield=13.11 gm (92%).

IR and NMR were identical with those of the product obtained in Example 1.

EXAMPLE 5

Synthesis of [2,8-bis(trifluoromethyl)-4-quinolinyl]-2-pyridinyl-methanone of formula 1

Repeating the procedure in Example 4 using aqueous tertiary butyl hydroperoxide, 70% (0.0572 mole, 7.36 ml) instead of hydrogen peroxide. Yield=13.04 gm (92.5%).

EXAMPLE 6

Synthesis of methanone 1 & nitrile compound 5

Repeating the procedure in Examples 1 and 3 using 4-bromo-quinoline 6 instead of 4-chloro derivative 3. Yield of compound 1=94%, yield of 5=97%.

EXAMPLE 7

Synthesis of methanone 1 & nitrile compound 5

Repeating the procedure in Example 6 using aqueous tertiary butyl hydroperoxide, 70% (0.0572 mole, 7.36 ml) instead of hydrogen peroxide. Yield of 1=93%; Yield of 5=95%.

What is claimed is:

1. A process for the preparation of methanone of formula 1, said process comprising the steps of:
  a) condensing a halo-quinoline with an α-picolyl derivative in the presence of an organic solvent, a base and a phase transfer catalyst at −10° to +90° C.;
  b) adding an oxidising agent to the reaction mixture of step (a) containing the acetonitrile derivative of formula 5 at −10° to +90° C.;
  c) cooling the reaction mixture of step (b) and neutralising with any suitable acid followed by extraction with an organic solvent, and
  d) removing the organic solvent and crystallizing the methanone of formula (1).

2. A process as claimed in claim 1 wherein in step (a) the haloquinoline derivative is selected from a group consisting of 4-chloro, 4-bromo, F4-Fluoro or 4-Iodo quinoline and preferably 4-chloroquinoline.

3. A process as claimed in claim 1 wherein in step (a) the α-picolyl derivative is selected from a group consisting of 2-pyridyl-acetonitrile, pyridyl-acetic acid esters and α-nitro-2-picoline and preferably 2-pyridyl acetonitrile.

4. A process as claimed in claim 1 wherein in step (a) the amount of α-picolyl derivative varies from 0.5 to 3.0 moles of haloquinoline used.

5. A process as claimed in claim 1 wherein step (a) the organic solvent used is of medium polarity.

6. A process as claimed in claim 1 wherein in steps (a) and (c) the organic solvents are selected from a group consisting tetrahydrofuran, diethyl ether, dioxane, 1,2-dichloroethane, 1,2 dichloromethane, chloroform, toluene, dimethyl formamide, dimethyl sulphoxide, ethers, or chlorohydrocarbons.

7. A process as claimed in claim 1 wherein in step (a) the organic solvent is tetrahydrofuran.

8. A process as claimed in claim 1 wherein the organic solvent used in steps (a) and (c) may be the same or different.

9. A process as claimed in claim 1 wherein the amount of organic solvent is in the range of 1:1 to 1:10 of haloquinoline used.

10. A process as claimed in claim 1 wherein the base is a powdered solid or 10% saturated solution of hydroxides, carbonates or acetates of alkali or alkaline earth metals and selected from sodium hydroxide, potassium hydroxide, magnesium, magnesium hydroxide, sodium carbonate, potassium carbonate, acetates of sodium, potassium or calcium, etc.

11. A process as claimed in claim 1 wherein in step (a) the amount of the base is 5 to 10 times in excess of haloquinoline or equivalent to the amount of haloquinoline.

12. A process as claimed in claim 1 wherein in step (a) the amount of base to haloquinoline is in the range of 5:1.

13. A process as claimed in claim 1 wherein in step (a) the phase transfer catalyst is capable of transferring the carbanion generated from pyridylacetonitrile represented by formula (4) or its analogues.

14. A process as claimed in claim 1 wherein the amount of the phase transfer catalyst varies form 1–10 mole % of haloquinoline used.

15. A process as claimed in claim 1 wherein in step (a) the phase transfer catalyst is selected from tetraalkylammonium or phosphonium salt of formula (8) wherein Y is nitrogen or phosphorous and $R^1$, $R^2$, $R^3$, and $R^4$ are identical or different and are alkyl groups with carbon 1 to 20 and X is $Cl^-$, $Br^-$, $I^-$, $HSO_4^-$ or other anions derived from inorganic acids such as sulfuric acid, phosphoric acid or tetrafluoroboric acid.

16. A process as claimed in claim 1 wherein in step (b) the oxidizing agent used is a reagent capable of providing peroxide ion.

17. A process as claimed in claim 1 wherein in step (b) wherein the oxidizing agent acts as a nucleophile agent.

18. A process as claimed in claim 1 in step (b) wherein the oxidising agent is selected from the group consisting of tertiary butyl peroxide, hydrogen peroxide, etc. examples or organic hydroperoxide, cumene hydroperoxide, ethylbenzene hydroperoxide; cyclohexane hydroperoxide; methylcyclohexane hydroperoxide; pinane hydroperoxide; tetrahydronaphthalene hydroperoxide; isobutylbenzene hydroperoxide; tetrahydronaphthalene hydroperoxide; isobutylbenzene hydroperoxide; isopropyl hydroperoxide; and/or ethylnaphthalene hydroperoxide.

19. A process as claimed in claim 1 wherein the oxidizing agent is hydrogen peroxide, tertiary butyl hydroperoxide and/or tert-amyl hydroperoxide.

20. A process as claimed in claim 1 wherein the amount of the oxidizing agent is 1 to 5 mole equivalents of haloquinoline used.

21. A process as claimed in claim 1 wherein the reaction is effected at a temperature range of −10° C. to +90° C.

22. A process as claimed in claim 1 wherein in step (c) the acid is selected from the group consisting of mineral acids or organic acids.

23. A process as claimed in claim 1 wherein the acid is ortho-phosphoric acid.

* * * * *